(12) United States Patent
Massironi

(10) Patent No.: US 7,867,517 B2
(45) Date of Patent: *Jan. 11, 2011

(54) ORAL PHARMACEUTICAL COMPOSITION WITH IMPROVED BIOAVAILABILITY

(75) Inventor: Maria Gabriella Massironi, London (GB)

(73) Assignee: Farmatron, Ltd., London (GB)

( * ) Notice: Subject to any disclaimer, the term of this patent is extended or adjusted under 35 U.S.C. 154(b) by 1171 days.

This patent is subject to a terminal disclaimer.

(21) Appl. No.: 10/482,460

(22) PCT Filed: Jun. 19, 2002

(86) PCT No.: PCT/EP02/06748

§ 371 (c)(1),
(2), (4) Date: Jul. 23, 2004

(87) PCT Pub. No.: WO03/002101

PCT Pub. Date: Jan. 9, 2003

(65) Prior Publication Data

US 2004/0247666 A1    Dec. 9, 2004

(30) Foreign Application Priority Data

Jun. 26, 2001   (IT) .................. MI2001A001338

(51) Int. Cl.
*A61K 9/14*   (2006.01)

(52) U.S. Cl. .................................. 424/484

(58) Field of Classification Search ............ 424/484, 424/486
See application file for complete search history.

(56) References Cited

U.S. PATENT DOCUMENTS

| | | | | |
|---|---|---|---|---|
| 4,786,495 A | * | 11/1988 | Bird et al. | 424/456 |
| 5,827,536 A | * | 10/1998 | Laruelle | 424/451 |
| 5,863,558 A | * | 1/1999 | Jao et al. | 424/465 |
| 5,993,858 A | | 11/1999 | Crison et al. | 424/490 |
| 6,056,944 A | * | 5/2000 | Finidori | 424/49 |
| 6,248,363 B1 | * | 6/2001 | Patel et al. | 424/497 |

FOREIGN PATENT DOCUMENTS

| | | | |
|---|---|---|---|
| WO | WO 97/18798 | * | 5/1997 |
| WO | WO 98/24430 | | 11/1998 |
| WO | WO 02/24172 | | 3/2002 |

OTHER PUBLICATIONS

Elmaleh et al. Probe into the physical properties of gelucire 44/14 pharmaceutical formulation.*
Sharma et al, J. Pharm. Sci 1995 Abstract only.*
Shah et al, Drug Dev. Ind. Pharm, 1999 25(1) 63-67 Abstract Only.*
Rajewski et al. J. Pharm. Scieces 85(11) 1996, 1142-1169.*

* cited by examiner

*Primary Examiner*—Robert C Hayes
*Assistant Examiner*—Shirley V Gembeh
(74) *Attorney, Agent, or Firm*—Porzio, Bromberg & Newman, P.C.

(57) ABSTRACT

The present invention relates to prompt-release oral pharmaceutical compositions containing one or more active principles solubilised, suspended or embedded in a suitably formulated amphiphilic matrix for improving in vitro and in vivo bioavailability of medicaments sparingly absorbed through the oral route and/or with problems of high variability of absorption in the gastrointestinal tract.

8 Claims, No Drawings

ORAL PHARMACEUTICAL COMPOSITION WITH IMPROVED BIOAVAILABILITY

RELATED APPLICATIONS

This is a National Stage of International Application Number PCT/EP02/06748, filed Jun. 19, 2002, which claims priority of Italy patent application MI2001A001338 filed Jun. 26, 2001.

The present invention relates to prompt-release oral pharmaceutical compositions containing one or more active principles solubilised, suspended or embedded in an amphiphilic matrix which is suitably formulated to increase in vitro and in vivo the bioavailability of medicaments sparingly absorbed through the oral route and/or with problems of high variability of absorption in the gastrointestinal tract.

Formulation of drugs in amphiphilic matrix systems, with other surfactants, superdisintegrants and other excipients which are used for obtaining pharmaceutical forms having suitable technological properties, allows to increase the in vitro dissolution rate, to improve bioavailability and to have less absorption variability.

The prompt-release compositions of the invention can contain active principles belonging to the therapeutic classes of analgesic, anti-inflammatory, antineoplastic, immunomodulating, antihemetic, antidiabetic, cardiovascular, hypnotic, tranquilizing, antihistamine drugs, antibiotics, antidepressant.

TECHNOLOGICAL BACKGROUND

Prompt-release, fast-absorption and improved bioavailable formulations can be prepared according to different known techniques:

Complexes and composites based on cyclodextrins or other polymers, in which the active ingredient has been loaded through solubilisation in water or other organic solvents, co-grinding to dryness or in organic solvents and/or freeze-drying.

Micronisation and amorphisation processes of the active ingredient.

Emulsions, microemulsions (W/O, O/W), multiple emulsions (W/O/W). Salification processes, even extemporary, or solubilization of the active ingredient as such or in conventional liquid formulations such as syrups, drops, solutions, soft-gelatin capsules, effervescent forms.

Organic solvents and/or cosolvents (such as dioxane, dimethylacetamide, dimethylsulfoxide, dimethyl isosorbide or binary or multiple systems consisting of diethylene glycol monoethyl ether with polyethylene glycols added with non-ionic surfactants.

All the above mentioned procedures suffer, however, from some drawbacks and disadvantages.

Complexes and composites based on cyclodextrins or other polymers require costly processes, which are often difficult to carry out and do not ensure complete complexation of the active ingredient; moreover the active ingredient to polymer ratio is often a limiting factor to the preparation of an easy-to-administer pharmaceutical form.

Micronisation processes do not always ensure significant increases in plasma levels, while increasing the apparent density/volumes and surface areas of the powders thus making the production of capsules, tablets and granulates troublesome.

Amorphisation processes, although improving the bioavailability of the drugs, induce recrystallization in the time and often also lower stability of the active ingredient, thus negatively affecting the quality of the medicament.

Emulsions and/or microemulsions, either simple or multiple, are often unstable and cannot carry pharmacologically active amounts of the medicament.

Salification and/or solubilization processes of conventional pharmaceutical forms sometime cannot improve the bioavailability of sparingly permeable and absorbable, or lipophilic, medicaments, due to reprecipitation of the active ingredient in the biological fluids, thus removing the advantage of a technological process aiming at dissolving the medicament in the pharmaceutical formulation.

Prompt-release, improved bioavailability formulations should ensure the standardization of the physical pharmaceutical state of the active ingredient, for fast release from the pharmaceutical form and to reduce any deviation from linear release.

DISCLOSURE OF THE INVENTION

This object has been attained according to the present invention, through the formulation of an amphiphilic matrix, single or complex, with other surfactants and/or cyclodextrins and/or superdisintegrants.

The compositions of the invention are characterized by a fast onset phase of the amount of drug which under sink conditions remains rapid until complete solubilization, dispersion and/or extemporaneous and/or in situ emulsification of the system, which quickly releases the active ingredient in the gastrointestinal tract.

The prompt-release oral pharmaceutical compositions present invention comprise:
1. a matrix consisting of amphiphilic compounds either liquid or with melting point below 60° C., possibly to form eutectic mixture melting at 35-37° C., in which the active ingredient is at least partially soluble and/or dispersed and/or embedded or granulated with amphiphilic compound previously solubilised or suspended in solvent (preferably water);
2. a surface acting component which is compatible with the amphiphilic matrix and can be homogeneously solubilized and/or dispersed therein;
3. a component based on cyclodextrins and/or superdisintegrants which can be dispersed in the surface-activated amphiphilic matrix or can in turn be loaded on the optionally surface-activated amphiphilic matrix, to obtain a liquid, semisolid or solid form;
4. any other excipients.

DETAILED DISCLOSURE OF THE INVENTION

The compositions of the invention can be obtained with a process which comprises the following steps:
a) adding surfactants to the amphiphilic matrix, to obtain a homogeneous solution or dispersion;
b) solubilizing, suspending, dispersing, totally or partly embedding one or more active principles;
c) adding cyclodextrins and/or superdisintegrants, or granulating or dispersing with cyclodextrins and/or polymers;
d) optionally adding excipients;
e) optionally film-coating with cellulose derivatives or methacrylic acid polymers.

More particularly, according to the present invention:
In step a) the surface-activated amphiphilic matrix is prepared. First any amphiphilic semisolid excipients or mixtures thereof are melted above 60° C., or solubilised or suspended in solvent (preferably water) to obtain a homogeneous solution and/or dispersion, which becomes again semisolid or solid at room temperature, with eutectic properties at temperatures ranging from 35° C. to 37° C. (body temperature) or able to be used as granulating system. Afterwards, said excipients, which have become liquid upon melting or are already liquid at room temperature, are added with surfactants to obtain a homogeneous dispersion.

In step b), the active ingredient is solubilised, dispersed and/or embedded in the surface-activated amphiphilic matrix from step a) to obtain a homogeneous solution and/or dispersion and/or granules.

In step c), the system from step (b) is added with different amounts of cyclodextrins and/or superdisintegrants until homogeneous dispersion. The resulting system can be distributed into soft- or hard-gelatin capsules to obtain a liquid, semisolid or solid pharmaceutical form inside the capsule. Alternatively, the system from step (b) can be loaded onto cyclodextrins and/or superdisintegrants and/or mixtures thereof to obtain powder, microgranules or granules having good free-flowing and/or tabletting characteristics.

In step d), excipients with different functions may be added to transform liquid or semisolid formulations into solid ones for the preparation of capsules, tablets, granulates, microgranules, minitablets, sachets, said excipients being, for example, silica, celluloses, starches, sugars, polyvinyl pyrrolidones, methacrylates, glidants, antiaggregants, lubricants such as magnesium stearate, stearic acid, talc, or the liquid semisolid formulations can be added with other liquid cosolubilizers, such as, water, polyethylene glycols, glycerin, sorbitol.

Other adjuvants can be selected from preservatives (parabens, benzalkonium chloride), mineral and organic acid/bases, antioxidizers (BHT, BHA, tocopherols), stabilizers (EDTA).

Amphiphilic compounds for use in the present invention comprise polar lipids (lecithin, phosphatidyl choline, phosphatidyl ethanolamine), ceramides, glycol alkyl ethers such as diethylene glycol monoethyl ether (Transcutol), macrogolglycerides consisting of mixtures of mono- di- and triglycerides and polyethylene glycols and fatty acids (gelucire 44/14; gelucire 50/13) mono and diesters, polyethylene glycols hydroxystearates (Solutol@ HS 15).

Surfactants for use in the present invention comprise phosphatides and lecithins (phosphatidyl cholines, phosphatidyl diethanolamines, sphyngomyelins), anionic and non-ionic emulsifying waxes, sodium lauryl sulfate, sodium dodecyl sulfate, polysorbates, cholic acids, poloxamer, sodium sulfosuccinate, sodium lauryl sarcosinate.

Cyclodextrins and superdisintegrants for use in the present invention comprise alpha-beta-gamma cyclodextrins, hydroxyethylcyclodextrins, methylcyclodextrins, hydroxypropylcyclodextrins, sodium starch glycolate (Explotab®), croscarmellose sodium (Acdisol®), cross-linked polyvinylpyrrolidone, Amberlites® (IRP 88).

According to a general embodiment of the invention, an amphiphilic matrix is first is prepared, which is added with one or more surfactants in amounts that usually do not exceed 10% w/w, preferably in amounts from 0.1% to 5%.

This mixture may be added with amounts of cyclodextrin or superdisintegrant of up to 10%, preferably from 0.1% to 2.5%, to obtain a homogeneous dispersion.

The active ingredient may be dissolved and/or dispersed in this system up to concentrations ranging from 0.1% to 50%, preferably from 0.1% to 4.9%. The resulting formulation may be used for filling into hard- or soft-gelatin capsules.

Alternatively, the liquid or semisolid amphiphilic matrix may be used as granulating component. Once melted, or solubilised/suspended in solvents (preferably water), this matrix containing part of the surfactants, dextrins, superdisintegrants and active ingredient solubilised or dispersed, can be added to a significant amount of superdisintegrants and/or cyclodextrins already containing the remainder of the active ingredient, to obtain a solid composition ready for filling into capsules or sachets, or for transformation into tablets with the addition of suitable adjuvants such as silica, microcrystalline celluloses, starches, lubricants. The semisolid amphiphilic matrix is cooled and subjected to extrusion and/or granulation, to make the formulation compact until obtaining an easy-to-process granule or microgranule. The final pharmaceutical form may be prepared by dry- or wet-granulation.

The capsules, microgranules and/or tablets can be subjected to conventional coating processes with gastro-soluble films or gastro-protected with cellulose and methacrylic polymers.

The active principles which can be conveniently formulated according to the invention comprise:

1. Antineoplastics and immunomodulators, such as: cyclophosphamide, chlorambucil, melfalan, busulfan, methotrexate, fludarabine, mercaptopurine, thioguanine, fluorouracil, tegafur, etoposide, idarubicin, procarbazine, estramustine, hydroxycarbamide, irinotecan, topotecan, tretinoin, medroxyprogesterone, megestrol, tamoxifen, toremifen, bicalutamide, flutamide, aminoglutetimide, anastrozole, exemestane, letrozole, levamisole, cyclosporin, micofenolate mofetil, tacrolimus, doxorubicin, epirubicin, dacarbazine, paclitaxel, daunorubicin, irinotecan and camptotecins.

2. Detoxicant compounds for cytostatic treatments, such as: calcium folinate, calcium levofolinate, folic acid.

3. Anti-inflammatories, analgesics and antirheumatics, such as: acetaminophen, phenacetin, sodium salicylate, acetametacin, diclofenac, fentiazac, indomethacin, proglumetacin, sulindac, cinnoxicam, meloxicam, piroxicam, tenoxicam, thiaprophenic acid, flurbiprofene, furprofene, ibuprofen, ketoprofen, naproxen, oxaprozin, mefenamic acid, niflumic acid, amtolmetin guacil, nabumetone, nimesulide, etodoloac, celecoxib, glucosamine and its salts.

4. Anti-inflammatories, Anti-ashmatics, such as: olsalazine, 5-aminosalicylic, sulfasalazine, budesonide, ciclesonide, betamethasone, beclomethasone, flunisolide, triamcinolone, mometasone.

5. Drugs for the treatment of bone diseases, such as: alendronic acid, clodronic acid, etidronic acid, risedronate, tiludronate.

6. Prostatic, such as: tamsulosin.

7. Anti-acne: tretinoin, isotretinoin.

8. Antivirals, such as: acyclovir, amprenavir, saquinavir, ritonavir.

9. Hormons and peptides: growth hormons, insuline, calcitonin, gosereline, leuprolide, buserelin, follitropin.

10. Ematological, such as: erithropoyetin, bromeline.

11. Antitussives, such as: dextromethorphan, codeine phosphate, levodropropizine.

12. Systemic antihistamines, such as: mequitazine, prometazine, cetrizine, oxatomide, acrivastatin, fexofenadine, ketotifene, loratadine, mizolastine, terfenadine.

13. Antiemetics, antinausea, such as: dolasetron, granisetron, ondansetron, tropisetron, proclorperazine.

14. Antipropulsives, such as: loperamide.

15. Oral hypoglycemizining antidiabetics, such as: metformin, chlorpropamide, glybenclamide, glyclazide, glymepiride, glypizide, glyquidone, glysolamide, pioglitazone, rosiglitazone.
16. Cathartics, such as: bisacodil, sodium picosulfate.
17. Antiepileptics, such as: vaiproate, carbamazepine, phenyloin, gabapentin, tiagabine, lamotrigine, topiramate, biperidene, bornaprine, metixene, procyclidine, trihexyphenidyl.
18. Alpha-Blockers, such as: doxazosin, terazosin, urapidil. Antihypertensives, ace-inhibitor, betablocker, antiarhitmic and coronarodilators, such as: captopril, labetalol, atenolol, propafenone isosorbide mono-dinitrate, quinapril, enalapril, candesartan ciletexil, amiodarone, valsartan, isradipine.
19. Calcium antagonists, such as: nifedipine, nicardipine, diltiazem, verapamil, amlodipine, felodipine.
20. Diuretics, such as: chlorthalidone, fenquizone, indapamide, metolazone, xipamide, bumetanide, furosemide, piretanide, toresamide, etozolin.
21. Hypolipemizing agents such as: atorvastatin, fluvastatin, pravastatin, simvastatin, lovastatin.
22. 5HT1 selective antagonists such as: rizatrepan, sumatripan, zolmitripan, pizotifen.
23. Antiparkinson drugs, such as: pergolide, carbidopa, levodopa, biperiden.
24. Antidepressant such as: paroxetine, fluvoxamine, fluoxetine, sertraline, mirtazapine.
25. Antibiotics such as: cefadroxil, ofloxacin, ciprofloxacin, doxycyclin, erytromycin, cefaclor, ampicillin, cephradine, doxacillin, cefuroxime axetil, amoxicillin, potassium clavulanate, clarithromicin, norfloxacin.

As far as dissolution characteristics are concerned, these formulations, when contacted with water or aqueous fluids, cause the prompt dispersion, solubilization and/or emulsification of the active ingredient present in the system. Surfactants, cyclodextrins and superdisintegrants present in the amphiphilic structure favor wettability of the system and homogeneous release of the active principles in solution, thus improving gastrointestinal absorption.

The following examples illustrate the invention in greater detail.

Example 1

500 g of gelucire 44/14 are melted at a temperature ranging from 55° C. to 65° C. The molten mass is added under strong stirring with 50 g of Etoposide to obtain a homogeneous solution/dispersion. The resulting mixture is added in succession under strong stirring with 5 g of sodium lauryl sulfate and 45 g of beta-cyclodextrins. The resulting mixture is left under stirring for at least 15 minutes, at a temperature of at least 55° C.; then hard-gelatin capsules, size 0 or double 0, are filled with a distributing syringe, to reach a 600 mg weight for single capsule.

Each capsule is then closed and sealed by spraying with 50% ethanol and water and subsequent heating under hot air to obtain the final capsule.

The resulting capsules have in vitro release not lower than 80% after 30 minutes according to the method described in USP/NF.

Example 2

500 g of gelucire 44/14 and 44 g of Solutol HS 15 are melted at a temperature ranging from 55° C. to 65° C. The molten mass is added under strong stirring with 2.5 g of Methotrexate to obtain a homogeneous solution/dispersion. The resulting mixture is added in succession under strong stirring with 10 g of sodium sulfosuccinate and 25 g of cross-linked polyvinylpyrrolidone (Kollidon® XL).

The resulting mixture is left under stirring for at least 15 minutes, at a temperature of at least 55° C.; then hard-gelatin capsules, size 0 or double 0, are filled with a distributing syringe, to reach a 550 mg weight for single capsule.

Each capsule is then closed and sealed by spraying with 50% ethanol and water and subsequent heating under hot air to obtain the final capsule.

The resulting capsules have in vitro release not lower than 75% after 45 minutes according to the method described in USP/NF.

Example 3

510 g of gelucire 44/14 are melted at a temperature ranging from 55° C. to 65° C., then added with 5 g of diethylene glycol monoethyl ether (Transcutol®). The molten mass is added under strong stirring with 30 g of Paclitaxel to obtain a homogeneous solution/dispersion. The resulting mixture is added in succession under strong stirring with 5 g of sodium lauryl sulfate and 30 g of beta-cyclodextrins. The resulting mixture is left under stirring for at least 15 minutes, at a temperature of at least 55° C.; then hard-gelatin capsules, size 0 or double 0, are filled with a distributing syringe, to reach a 580 mg weight for single capsule.

Each capsule is then closed and sealed by spraying with 50% ethanol and water and subsequent heating under hot air to obtain the final capsule.

The resulting capsules have in vitro release not lower than 75% after 45 minutes in a dissolution bath containing 900 ml of 0.1N hydrochloric acid with rotating paddle at 50 rpm.

Example 4

100 g of gelucire 44/14 are melted at a temperature ranging from 55° C. and 65° C. together with a 5 g of Solutol HS15. The molten mass is added under strong stirring with 50 g of Nimesulide to obtain a homogeneous dispersion. The resulting mixture is added with 4 of sodium dodecylsulfate under strong stirring.

400 g of cross-linked polyvinylpyrrolidone and 50 g of Nimesulide are loaded into a granulator/homogenizer. The mass is mixed for at least 15 minutes. The molten mass prepared above is loaded into the granulator containing polyvinylpyrrolidone and Nimesulide and the components are mixed to obtain a homogeneous granulate. The resulting granules are normalized, then loaded in a mixer, adding in succession 100 g of microcrystalline cellulose, 0.5 g of magnesium stearate and 0.5 g of colloidal silica.

After mixing for 5 minutes, the final mixture is tableted to unitary weight of 710 mg/tablet. The resulting tablets were subjected to dissolution test in simulated gastric juices, showing a release of the active ingredient not lower than 75% after 45 minutes.

Example 5

50 g of gelucire 50/13 are melted at a temperature ranging from 60° C. to 65° C. The molten mass is added under strong stirring with 25 g of Ketoprofen to obtain a homogeneous dispersion. The resulting mixture is added with 4 of sodium lauryl sulfate under strong stirring.

405 g of crosscarmellose sodium (Ac-di-Sol®) and 25 g of Ketoprofen are loaded into a granulator/homogenizer. The mass is mixed for at least 15 minutes. The molten mass prepared above is loaded into the granulator containing Ac-di-Sol® and Ketoprofen and the components are mixed to obtain a homogeneous granulate. The resulting granules are normalized, then loaded in a mixer, adding in succession 125 g of microcrystalline cellulose, 1 g of magnesium stearate and 25 g of colloidal silica. After mixing for 5 minutes, the final mixture is tabletted to unitary weight of 660 mg/tablet. The resulting tablets were subjected to dissolution test in simulated gastric juices, showing a release of the active ingredient not lower than 80% after 45 minutes.

Example 6

500 g of gelucire 44/14 are melted at a temperature ranging from 55° C. to 65° C. The molten mass is added under strong stirring with 25 g of Calcium Folinate to obtain a homogeneous solution/dispersion. The resulting mixture is added in succession with 5 g of lecithins and 5 g of beta-cyclodextrins under strong stirring. The resulting mixture is left under stirring for at least 15 minutes, at a temperature of at least 55° C.; then hard-gelatin capsules, size 0, are filled with a distributing syringe, to reach a weight of 540 mg for single capsule. Each capsule is then closed and sealed by spraying with 50% ethanol and water and subsequent heating under hot air to obtain the final capsule. The resulting capsules have in vitro release not lower than 80% after 30 minutes.

The invention claimed is:
1. Oral prompt-release pharmaceutical composition for the improved oral absorption of active ingredients, consisting essentially of:
   a) active ingredient;
   b) a macrogolglyceride matrix in combination with diethylene glycol monoethyl ether or polyethylene glycol hydroxystearate, forming a eutectic mixture melting at 35-37° C., in which the active ingredient is at least partially soluble and/or dispersed and/or embedded or granulated with said macrogolglycerides previously solubilized or suspended in solvent;
   c) a surface acting component selected from phosphatidyl choline, lecithin, poloxamer, sodium lauryl sulfate, sodium sulfosuccinate, or sodium dodecyl sulfate;
   d) cyclodextrin and/or superdisintegrant, that is dispersed in or is loaded on the matrix, to obtain a liquid, semisolid or solid form, wherein the superdisintegrant is selected from sodium starch glycolate, croscarmellose sodium, Amberlite or cross-linked polyvinylpyrrolidone; and
   e) optionally one or more excipients selected from silica, celluloses, starches, sugars, polyvinyl pyrrolidones, methacrylates, glidants, antiaggregants, lubricants, magnesium stearate, stearic acid, and talc, wherein said composition displays prompt-release of the active ingredient.

2. The composition as claimed in claim 1 wherein the solvent is water that the macrogolglycerides are previously solubilised or suspended within.

3. The composition as claimed in claim 1 wherein cyclodextrin comprises alpha-beta-gamma cyclodextrin, hydroxyethylcyclodextrin, methylcyclodextrin, or hydroxypropylcyclodextrin.

4. The composition as claimed in claim 1, wherein the superdisintegrant comprises Amberlite.

5. The composition as claimed in claim 1, wherein the active ingredient is in part present in the macrogolglyceride matrix and in part loaded on the cyclodextrin and/or superdisintegrant, in the form of minitablets or microgranules.

6. The composition as claimed in claim 1, wherein the active ingredient belongs to therapeutical categories selected from antineoplastics, immunomodulators, detoxicant compounds for cytostatic treatments, anti-inflammatories, analgesics, antirheumatics, drugs for the treatment of bone diseases, antitussives, systemic antihistamines, antiemetics, antinausea agents, antipropulsives, oral hypoglycemizing antidiabetics, cathartics, antiepileptics, alpha-blockers, diuretics, hypolipemizing agents, and 5HT1 selective antagonists.

7. The composition as claimed in claim 6, wherein the active ingredient is selected from the ingredients consisting of etoposide, calcium folinate, methotrexate, procarbazine, fluorouracil, idarubicin, cyclophosphamide, cyclosporin, topotecan, glypizide, glybenclamide, flutamide, nimesulide, piroxicam, and ketoprofen.

8. A pharmaceutical composition for the improved oral absorption of active ingredients, comprising:
   a) active ingredient;
   b) amphiphilic matrix in combination with diethylene glycol monoethyl ether or polyethylene glycol hydroxystearate, consisting of compounds either liquid or with melting point below 60° C., wherein the active ingredient is at least partially soluble and/or dispersed and/or embedded in the amphiphilic matrix;
   c) surface acting component which is compatible with the amphiphilic matrix and is homogeneously solubilized and/or dispersed therein; and
   d) cyclodextrin and/or superdisintegrant that is dispersed in the surface-activated amphiphilic matrix or is loaded on the surface-activated amphiphilic matrix, to obtain a liquid or semisolid form;
   wherein said composition is formulated for prompt-release of the active ingredient from the amphilic matrix and is a liquid or semi-solid.

* * * * *